(12) United States Patent
Laske et al.

(10) Patent No.: US 9,345,528 B2
(45) Date of Patent: May 24, 2016

(54) LARGE AREA CRYOABLATION CATHETER WITH MULTI-GEOMETRY TIP ECG/CRYO MAPPING CAPABILITIES

(75) Inventors: Timothy G. Laske, Shoreview, MN (US); Claudia Lueckge, L'ile-Bizard (CA); Réal Ste-Marie, Notre-Dame-de-L'Ile-Perrot (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 1131 days.

(21) Appl. No.: 13/360,379

(22) Filed: Jan. 27, 2012

(65) Prior Publication Data
US 2013/0197498 A1    Aug. 1, 2013

(51) Int. Cl.
A61B 18/04    (2006.01)
A61B 18/02    (2006.01)
A61B 18/14    (2006.01)
A61B 17/32    (2006.01)
A61B 18/18    (2006.01)
A61B 18/00    (2006.01)

(52) U.S. Cl.
CPC .............. *A61B 18/02* (2013.01); *A61B 18/1492* (2013.01); *A61B 17/320068* (2013.01); *A61B 18/1815* (2013.01); *A61B 2018/00101* (2013.01); *A61B 2018/00196* (2013.01); *A61B 2018/00357* (2013.01); *A61B 2018/00577* (2013.01); *A61B 2018/00613* (2013.01); *A61B 2018/0212* (2013.01); *A61B 2018/0262* (2013.01); *A61B 2018/1407* (2013.01); *A61B 2090/0463* (2016.02)

(58) Field of Classification Search
CPC ............... A61B 18/1447; A61B 18/02; A61B 2018/0212
USPC .......................................................... 606/22
See application file for complete search history.

(56) References Cited

U.S. PATENT DOCUMENTS

| | | | |
|---|---|---|---|
| 5,487,757 A | 1/1996 | Truckai et al. | |
| 5,520,682 A | 5/1996 | Baust et al. | |
| 6,064,902 A | 5/2000 | Haissaguerre et al. | |
| 6,106,518 A | 8/2000 | Wittenberger et al. | |
| 6,161,543 A * | 12/2000 | Cox et al. ...................... | 128/898 |

(Continued)

FOREIGN PATENT DOCUMENTS

| | | |
|---|---|---|
| CA | 2796267 A1 | 10/2011 |
| CN | 1075248 A | 8/1993 |
| WO | 2010135602 A1 | 11/2010 |

OTHER PUBLICATIONS

CIPO, PCT/CA2012/001160, Feb. 22, 2013 International Search Report, pp. 1-4.

(Continued)

*Primary Examiner* — Theodore Stigell
*Assistant Examiner* — Natasha Patel
(74) *Attorney, Agent, or Firm* — Christopher & Weisberg, P.A.

(57) ABSTRACT

A medical device including an ablation element. A thermally insulative sheath is included disposed within the ablation element. A fluid injection tube is disposed within a portion of the thermally insulative sheath. The ablation element passively transitions from a substantially linear geometric configuration to a substantially circular geometric configuration as the sheath is retracted proximally from a first position in which the sheath substantially encloses the fluid injection tube to a second position in which a portion of the fluid injection tube extends a distance away from the sheath.

18 Claims, 7 Drawing Sheets

(56) References Cited

U.S. PATENT DOCUMENTS

| | | | |
|---|---|---|---|
| 6,200,315 B1* | 3/2001 | Gaiser et al. | 606/41 |
| 6,241,722 B1 | 6/2001 | Dobak et al. | |
| 6,925,318 B2 | 8/2005 | Bencini | |
| 7,004,938 B2* | 2/2006 | Ormsby | A61B 18/1492 606/33 |
| 7,087,053 B2 | 8/2006 | Vanney | |
| 7,387,629 B2 | 6/2008 | Vanney et al. | |
| 7,575,566 B2 | 8/2009 | Scheib | |
| 7,794,454 B2 | 9/2010 | Abboud et al. | |
| 8,043,288 B2 | 10/2011 | Dando et al. | |
| 2002/0065515 A1 | 5/2002 | Falwell et al. | |
| 2002/0068901 A1 | 6/2002 | Werneth | |
| 2003/0171742 A1 | 9/2003 | Mihalik et al. | |
| 2004/0039371 A1* | 2/2004 | Tockman | A61M 25/0147 604/528 |
| 2005/0027289 A1 | 2/2005 | Castellano et al. | |
| 2006/0161146 A1 | 7/2006 | Cornelius et al. | |
| 2007/0156114 A1 | 7/2007 | Worley et al. | |
| 2008/0294158 A1 | 11/2008 | Pappone et al. | |
| 2010/0069734 A1 | 3/2010 | Worley et al. | |
| 2010/0114093 A1 | 5/2010 | Mahapatra et al. | |
| 2010/0249766 A1 | 9/2010 | Saadat | |
| 2011/0276075 A1 | 11/2011 | Fung et al. | |
| 2011/0313417 A1 | 12/2011 | De La Rama et al. | |
| 2012/0109116 A1* | 5/2012 | Asconeguy et al. | 606/21 |
| 2012/0265186 A1* | 10/2012 | Burger et al. | 606/21 |
| 2013/0103026 A1* | 4/2013 | Kleshinski et al. | 606/41 |

OTHER PUBLICATIONS

CIPO, PCT/CA2012/001160, Feb. 22, 2013 Written Opinion, pp. 1-3.

Supplementary European Search Report dated Sep. 25, 2015 for Application No. EP 12866676.5, 4 pages.

Notice On The First Office Action with Search Report and Text of Office Action included, dated Feb. 1, 2016, Patent Application No. 201280068093.0, Applicant: Medtronic CryoCath LP, 11 pages.

* cited by examiner

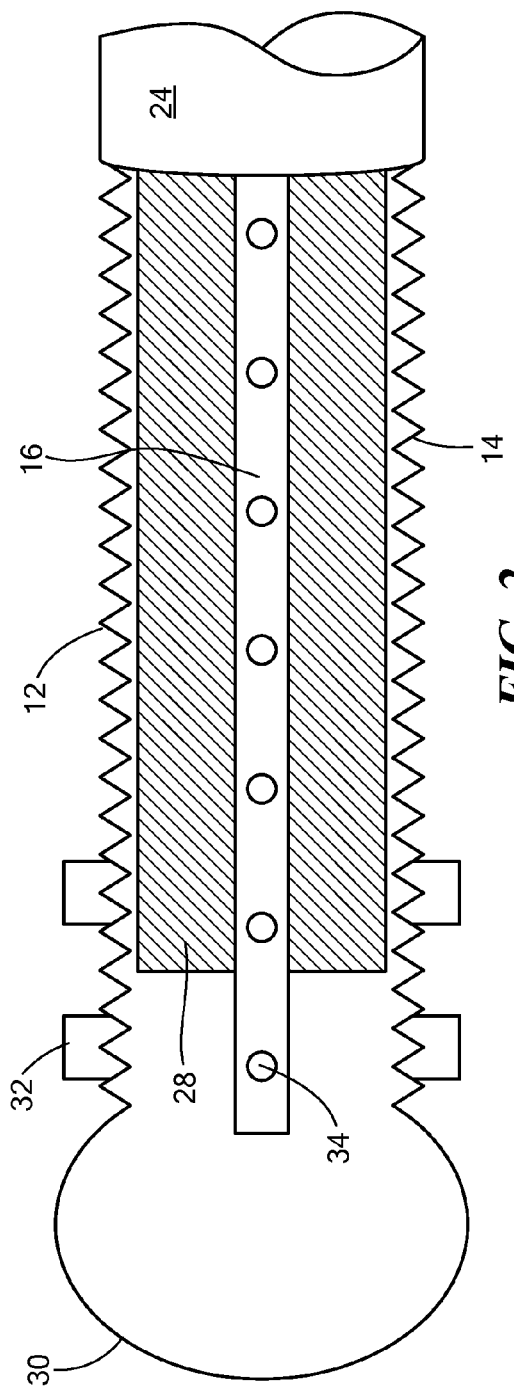
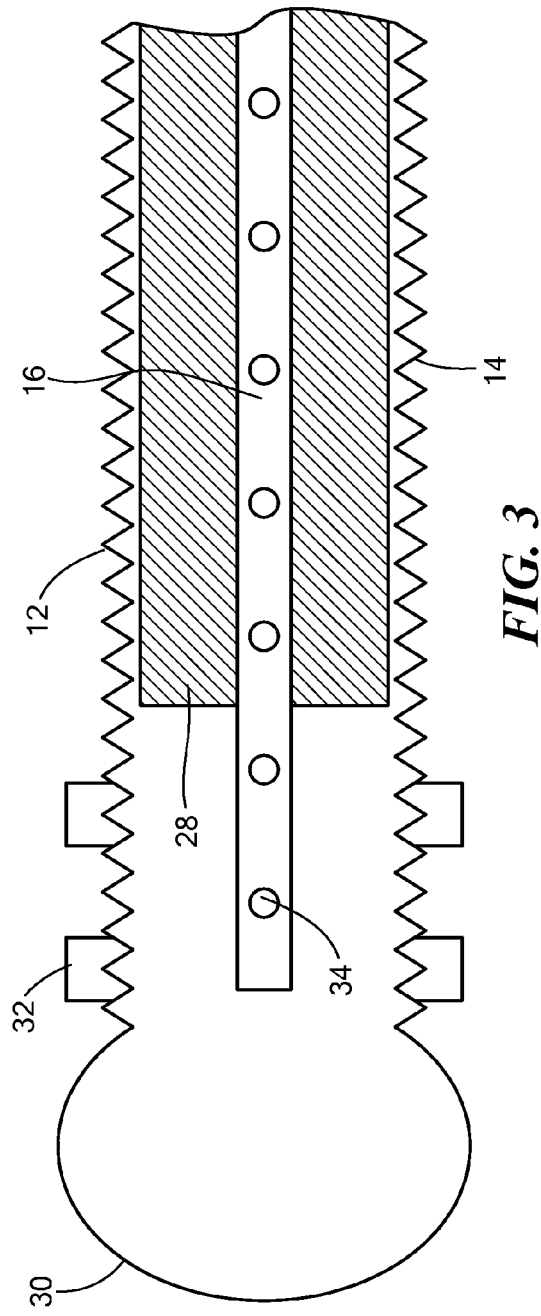
FIG. 2
FIG. 3

LARGE AREA CRYOABLATION CATHETER WITH MULTI-GEOMETRY TIP ECG/CRYO MAPPING CAPABILITIES

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and device for ablating cardiac tissue, and in particular, an ablation element defining multiple geometric configurations.

BACKGROUND OF THE INVENTION

Minimally invasive devices, such as catheters, are often employed for medical procedures, including those involving cardiac ablation. In a particular situation, an ablation procedure may involve creating a series of inter-connecting or otherwise continuous lesions in order to electrically isolate tissue believed to be the source of an arrhythmia. Such lesions may be created using a variety of different energy transmission modalities, such as cryogenic freezing.

Catheters or devices using cryogenic cooling may be used to lower the temperature of tissue, such as cardiac wall tissue, to an extent such that signal generation or conduction temporarily ceases and allows one to map or confirm that the catheter is positioned at a particular lesion or arrhythmogenic site. Cryogenic catheters may also operate at lower temperatures for ablation treatment, e.g., to cool the tissue to a level at which freezing destroys the viability of the tissue, and, in the case of cardiac tissue, permanently removes it as a signal generating or signal conducting locus.

Whether or not a particular treatment is successful may depend greatly on the qualities or characteristics of the lesion, such as its depth, uniformity, location, or the like. For example, for a given cardiac arrhythmia, a particular lesion depth and shape may be required to effectively obstruct the unwanted signal transmission through the problematic tissue region. Current cryogenic ablation devices create lesions by transfer of heat from the target tissue to either a balloon filled with cryogenic fluid or a substantially linear catheter tip. By using pull wires to deflect the distal end of the ablation device and/or regulating the inflation rate of the balloon, the size and shape of the treatment end of the ablation device may be imprecisely modified to create a desired shape of the ablation element for the particular lesion to be formed. However, such modifications are done during a particular procedure, not before, and require the skill of the surgeon using the ablation device to determine how to modify the treatment end of the ablation to create the desired lesion. Furthermore, such ablation devices have fixed ablation elements, whether a distal tip for creation of a focal lesion or balloon for a creation of a circumferential lesion, but not both.

Accordingly, there remains a need for medical devices that have ablation elements that are pre-fabricated to desired shapes to improve lesion formation, minimize error, reduce procedure time, and that are transitionable to different shapes and sizes depending on the type and location of the lesion to be created with minimal skill needed by the surgeon.

SUMMARY OF THE INVENTION

The present invention advantageously provides for a medical device including an ablation element. A thermally insulative sheath is included disposed within the ablation element. A fluid injection tube is disposed within a portion of the thermally insulative sheath. The ablation element passively transitions from a substantially linear geometric configuration to a substantially circular geometric configuration as the sheath is retracted proximally from a first position in which the sheath substantially encloses the fluid injection tube to a second position in which a portion of the fluid injection tube extends a distance away from the sheath.

In another embodiment, the medical device includes a cryogenic ablation element. A thermally insulative sheath is included disposed within the cryogenic ablation element. A fluid injection tube is disposed within a portion of the thermally insulative sheath and in fluid communication with a cryogenic fluid source, the fluid injection tube defines a plurality of fluid injection ports. The sheath seals at least one of fluid injection ports when advanced toward a distal portion of the cryogenic ablation element. The cryogenic ablation element passively transitions from a substantially linear geometric configuration to a substantially circular geometric configuration as the sheath is retracted proximally from a first position in which the sheath substantially encloses the fluid injection tube to a second position in which a portion of the fluid injection tube extends a distance away from the sheath.

In yet another embodiment, the medical device includes a cryogenic ablation element including a bellows portion. A thermally insulative sheath is movably disposed within the cryogenic ablation element. A fluid injection tube is disposed within a portion of the thermally insulative sheath and in fluid communication with a cryogenic fluid source, the fluid injection tube defines a plurality of fluid injection ports, and at least a portion of the fluid injection tube is biased in a substantially circular configuration. The sheath seals at least one of fluid injection ports when advanced toward a distal portion of the cryogenic ablation element. The sheath is stiffer than the fluid injection tube. The cryogenic ablation element passively transitions from a substantially linear geometric configuration to a substantially curvilinear geometric configuration, and passively transitioning from the substantially curvilinear geometric configuration to a substantially circular geometric configuration as the sheath is retracted proximally from a first position in which the sheath substantially encloses the fluid injection tube to a second position in which a portion of the fluid injection tube extends a distance away from the sheath.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 is a side cross-sectional view of a sheath of the medical device in FIG. 1 being retracted and exposing the distal tip;

FIG. 3 is a side cross-sectional view of a sheath of the medical device in FIG. 2 being further retracted and exposing the distal tip;

DETAILED DESCRIPTION OF THE INVENTION

Figure 1:
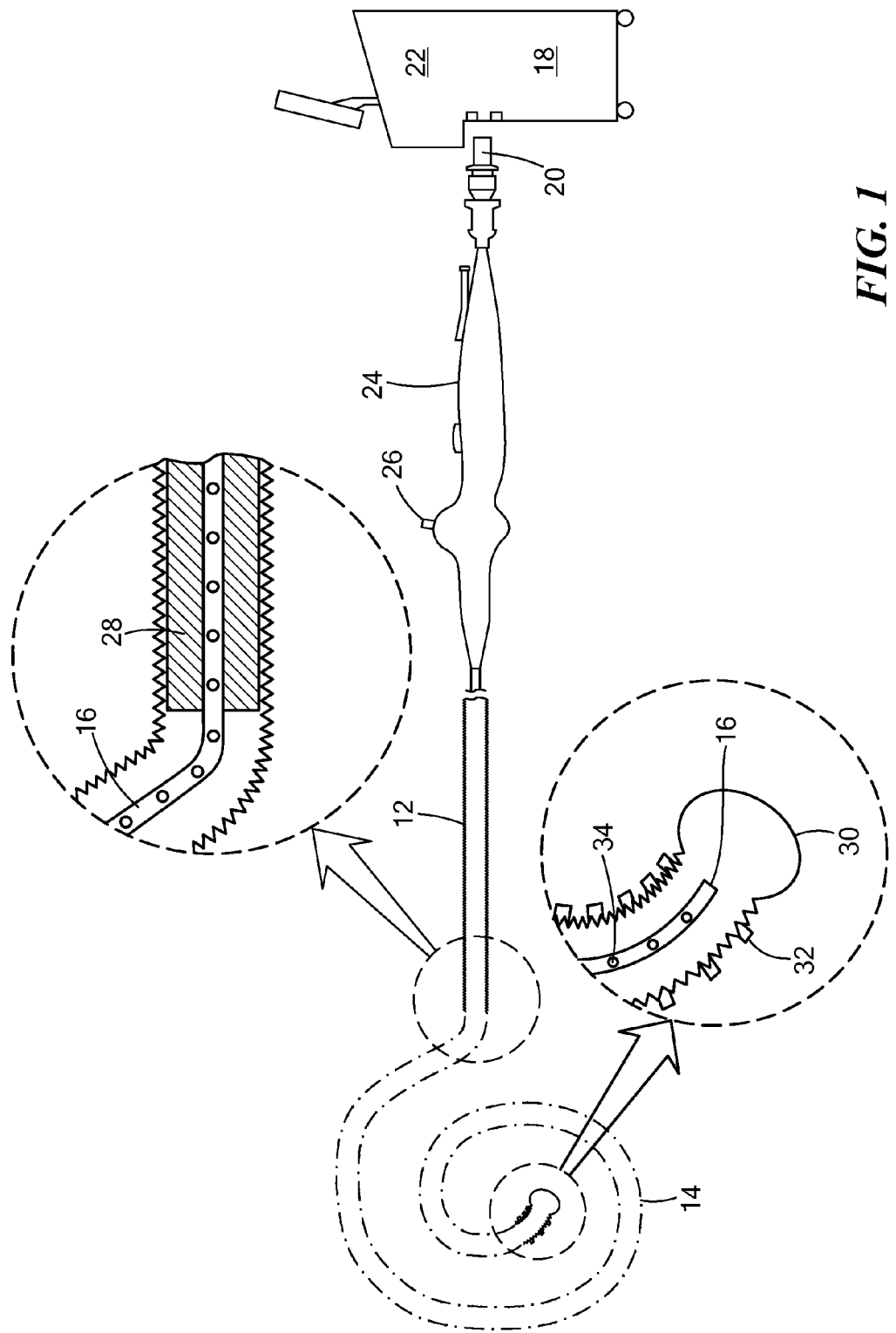
FIG. 1 is a system view of an exemplary medical device constructed in accordance with the principles of the present invention.

Now referring to the drawings in which like reference designators refer to like elements, there is shown in FIG. 1 an exemplary medical device and system constructed in accordance with the principles of the present invention, the medical device being designated generally as "10." Of note, the medical device 10 components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention.

The medical device 10 may be sized to be inserted into the vasculature, or alternatively, may be sized to be utilized on surface tissue, for example, for epicardial ablation or other cardiac treatment procedures. In a particular configuration, the medical device 10 may include a treatment element 12 defining a proximal portion and a distal portion, and may further include one or more lumens disposed within thereby providing mechanical, electrical, and/or fluid communication between the proximal and distal portions portion of the treatment element 12. The treatment element 12 may be composed of a thermally conductive material to transfer or receive thermal energy in the form of heat to or from the surrounding tissue. In an exemplary embodiment, the treatment element 12 is a cryogenic ablation element. In other embodiments, the treatment element 12 may be other ablation elements, for example, radiofrequency, electroporation, microwave, or acoustic ablation elements.

The treatment element 12 may be composed of a flexible metallic material. For example, the treatment element 12 may include a bellows portion 14 at a distal portion such that the distal portion may be flexed into a myriad of shapes and provide a large surface area for contact with a tissue region to be treated. Optionally, the bellows portion 14 may be commensurate in area with the treatment element 12 such that the bellows portion 14 spans substantially the entire length of the treatment element 12. In other embodiments, the treatment element 12 may define a tightly wound flat coil structure having a fluid tight seal between each winding in the coil.

The distal portion of the treatment element 12 may further be pre-fabricated to be biased in particular geometric configurations for particular treatment procedures. For example, the distal portion of the treatment element 12 may be biased in a substantially circular geometric configuration, helical, curvilinear, or any other geometric configuration or combinations of geometric configurations. In a particular configuration, the distal portion of the treatment element 12 defines at least one substantially circular geometric configuration such that a substantially circumferential lesion may be created when the distal portion of the treatment element 12 is placed in contact with tissue to be treated. In other configurations, for example, the distal portion of the treatment element 12 is biased to define at least one substantially circular geometric configuration and further biased to define a substantially helical geometric configuration at a position proximal the substantially circular configuration.

The treatment element 12 may include a fluid injection tube 16 and an exhaust lumen defining a fluid flow path there through. The fluid injection tube 16 may be composed of flexible material, for example, nitinol or nylon, and may be biased in particular geometric configurations. For example, the fluid injection tube 16 may be biased in a substantially circular configuration at its distal end. The fluid injection tube 16 may further be in fluid communication with a cryogenic fluid source 18 via one or more connectors 20. In addition, the treatment element 12 may include a guidewire lumen movably disposed within and/or extending along at least a portion of the length of the treatment element 12 for over-the-wire applications. To control the rate and volume of cryogenic fluid through the fluid injection tube 16, the system may include a control unit 22 coupled to a medical device 10 through the umbilical 20. The system may also include one or more sensors to monitor the operating parameters throughout the system, including for example, pressure, temperature, flow rates, volume, or the like in the control unit 22 and/or the medical device.

The medical device 10 may include a handle 24 coupled to the proximal portion of the treatment element 12. The handle 24 may include an element such as a lever 26 or knob for manipulating the treatment element 12 and/or additional components of the medical device 10. For example, a pull wire with a proximal end and a distal end may have its distal end anchored to the treatment element 12 at or near the distal end. The handle 24 can further include circuitry for identification and/or use in controlling of the medical device 10 or another component of the system. For example, the handle 24 may include one or more pressure sensors to monitor the fluid pressure within the treatment element 12. The handle 24 may be any shape or size depending on whether the medical device 10 is be used epicardially or within the vasculature.

Continuing to refer to FIG. 1, the medical device 10 may include a thermally insulative sheath or tubular element 28 sized to be slideably received within, or movable about, the treatment element 12. In an exemplary configuration, the fluid injection tube 16 is disposed within the sheath 28. The sheath 12 may be composed of thermally insulative material and may be movably affixed to a portion of the handle 24. In an exemplary configuration, the length of the sheath 28 is substantially the commensurate with the length of the treatment element 12 and/or fluid injection tube 16 such that sheath 28 may be entirely disposed within the treatment element 12. The sheath 28 may further have a greater stiffness than the stiffness than the treatment element 12 and/or the fluid injection tube 16, such that when the sheath 28 is completely advanced within the treatment element 12, the treatment element 12 does not bend or flex or bend. For example, the distal portion of the treatment element 12 and/or the fluid injection tube 16 may be biased in a substantially circular geometric configuration. As the sheath 28 is advanced within the treatment element 12 toward the distal portion of the treatment element 12, the sheath 28 operates to prevent flexion of the treatment element 12 and/or the fluid injection tube 16. As the sheath 28 is retracted such that a portion of the fluid injection tube 16 is exposed, the bias of the fluid injection 16, for example, may flex the treatment element 12 to a predetermined configuration.

Continuing to refer to FIG. 1, the distal portion of the treatment element 12 may include a distal tip 30. The distal tip 30 may also include electrically conductive portions or electrodes 32 disposed on or otherwise situated about the treatment region 12. The electrodes 32 may be in communication with a radiofrequency generator or power source such that impedance and/or other measurements such as complex fractionated electrograms may be obtained from the measure of electrical activity from the electrodes 32. For example, as shown in FIG. 1, the electrodes 32 may be deposited or placed onto an exterior surface of the treatment element 12 such that the electrodes 32 are positionable in proximity to a tissue site for subsequent treatment or diagnostic procedures. In particular, because the electrodes 32 may be positioned adjacent to each other, bipolar radiofrequency energy can be transmitted between the electrodes 32 to measure electrical activity between the electrodes 32 or transmit radiofrequency energy to the target tissue. In such a configuration, a surgeon can map the tissue region to be treated to determine which geometric configuration of the treatment element 12 to be used and the distance the sheath 12 may be retracted from the distal end of the treatment element 12 to create the desired geometric configuration.

Continuing to refer to FIG. 1, the fluid injection tube 16 may further include a plurality of fluid injection ports 34 to disperse cryogenic fluid out into the lumen of the treatment element 12. The fluid injection ports 34 may be arranged in any pattern along the outer diameter of the injection tube 16. For example, the plurality of injection ports 34 may be axially disposed along the major longitudinal axis of the fluid injection tube 16 or may be radially disposed to provide for a particular spray distribution of cryogenic fluid. In an exemplary configuration, as the sheath 28 is advanced over the fluid injection tube 16, the sheath 28 seals one or more of the fluid injection ports 34. As such, when cryogenic fluid is circulated through the fluid injection tube 16 toward the treatment element 12, a particular segment of the treatment element 12 may be cooled depending on the position of the sheath 28. For example, in a configuration where the sheath 28 is fully advanced, no fluid injection ports 24 are open. As the sheath 28 is retracted, the fluid injection ports 34 are unsealed such that cryogenic fluid may cool the treatment element 12 for a particular procedure.

Now referring to FIG. 2, the sheath 28 may be retracted, either manually by the surgeon by sliding back the sheath or through actuation of an actuator such as a pull wire, from a most distal position in which the sheath 28 substantially covers the fluid injection tube 16, such that no thermal energy transfer occurs at the distal end, to a position in which a portion of the distal portion of the fluid injection tube 16 is exposed facilitating the flow of cryogenic fluid out through the fluid injection ports 24 into the treatment element 12. The sheath 28 may further be retracted into the handle 24 and be attached directly to an actuator. Optionally, the sheath 28 may be composed of a shape memory alloy made of nickel-titanium. In such a configuration, the sheath 28 may be advanced or retracted contract (typically 2% to 10% of its) like muscles when electrically driven or heated to provide for small movements of the sheath 28 at the distal end. In another configuration, the sheath 28 may be retracted and advanced using pull wires for coarse adjustment of the sheath 28 and retracted and advanced by application of a low current to the sheath 28 for fine adjustment. The size and shape of the treatment element 12 in such a geometric configuration shown in FIG. 2 may be sufficient to create small spot lesions in the heart to treat atrial fibrillation, or other tissues.

Now referring to FIG. 3, the sheath 28 may be manually or automatically retracted to a position with respect to the treatment element 12, such that fluid injection tube 16 is exposed to a distance further away from the sheath 28 than the embodiment shown in FIG. 2. In such a configuration, the fluid injection tube 16 may impart a force on the treatment element 12 such that the treatment element 12 may define a substantially linear or curvilinear configuration depending on the distance the sheath 28 is retracted away from the distal end of the treatment element 12. For example, the sheath 28 may be retracted a few millimeters proximal the treatment element 12, such that the treatment element 12 defines a substantially linear configuration to perform particular ablation treatments. For example, a substantially linear ablation element 12 may be used for flutter and/or mitral line endocardial ablations.

Figure 4:
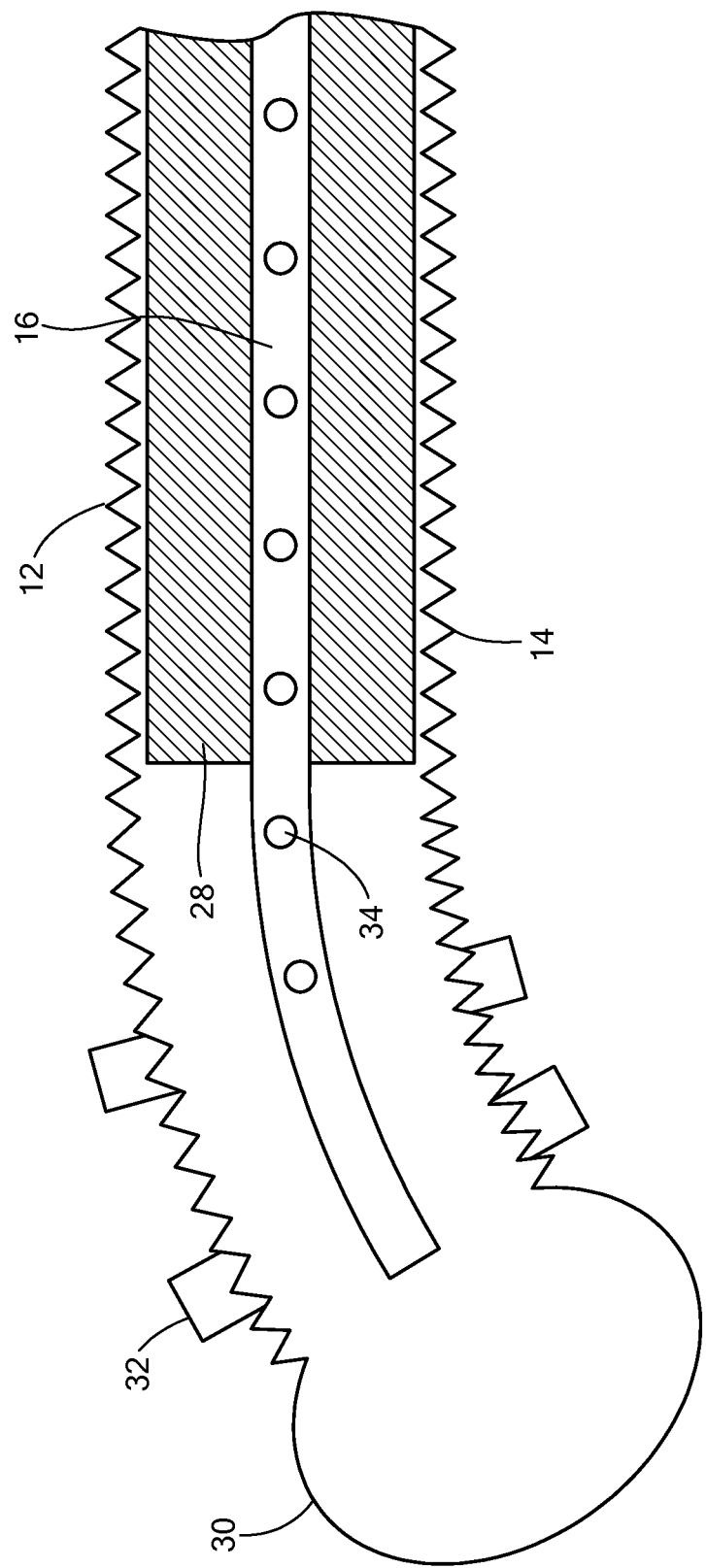
FIG. 4 is a side cross-sectional view of a sheath of the medical device in FIG. 3 being further retracted and exposing the distal tip.

Now referring to FIG. 4, as the sheath 28 is retracted proximally, the treatment element 12 may bend and/or deform owing the fluid injection tube 16 partially returning to its biased state. For example, as the sheath 28 is retracted from a position in which the treatment element 12 defines a substantially linear geometric configuration, the treatment element 12 may partially and passively transition into a substantially curvilinear configuration for particular ablation treatments. The deformation may occur, in part, because as the biased substantially circular portion of the fluid injection tube 16 is stretched it applies a torque on the treatment element 12, causing the treatment element 12 to define a curvilinear geometric configuration as the sheath 28 is retracted. When the treatment element 12 defines the geometric configuration shown in FIG. 4 it may also be sufficiently flexible to be flexed and applied substantially linearly for a roof line ablation. As the sheath 28 is further retracted, the treatment element 12 may continue to passively flex and transition to a more pronounced curved geometric formation (FIG. 5) such that a flutter or mitral line ablation may be performed.

Figure 5:
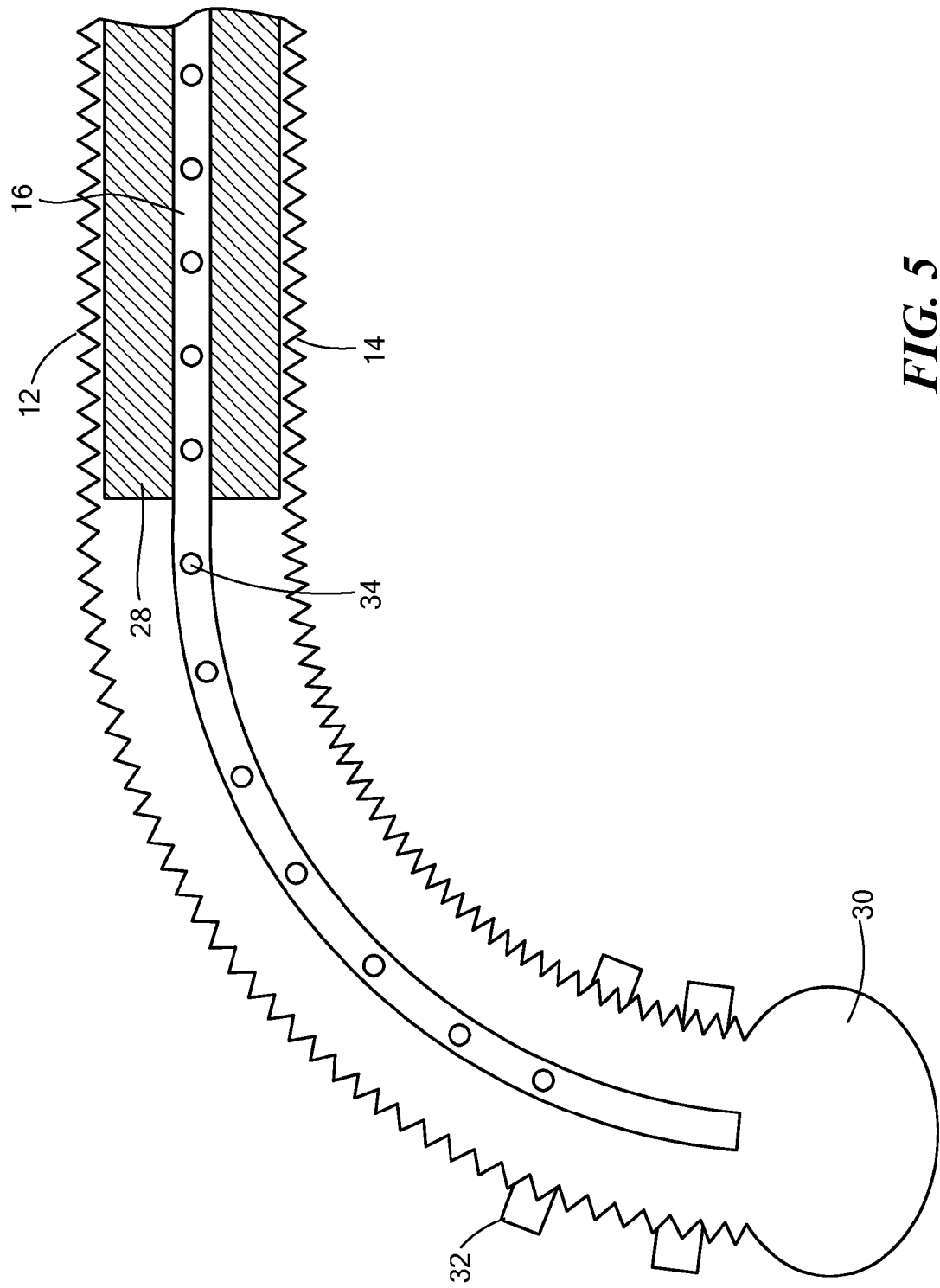
FIG. 5 is a side cross-sectional view of a sheath of the medical device in FIG. 4 being further retracted and exposing the distal tip.
Figure 6:
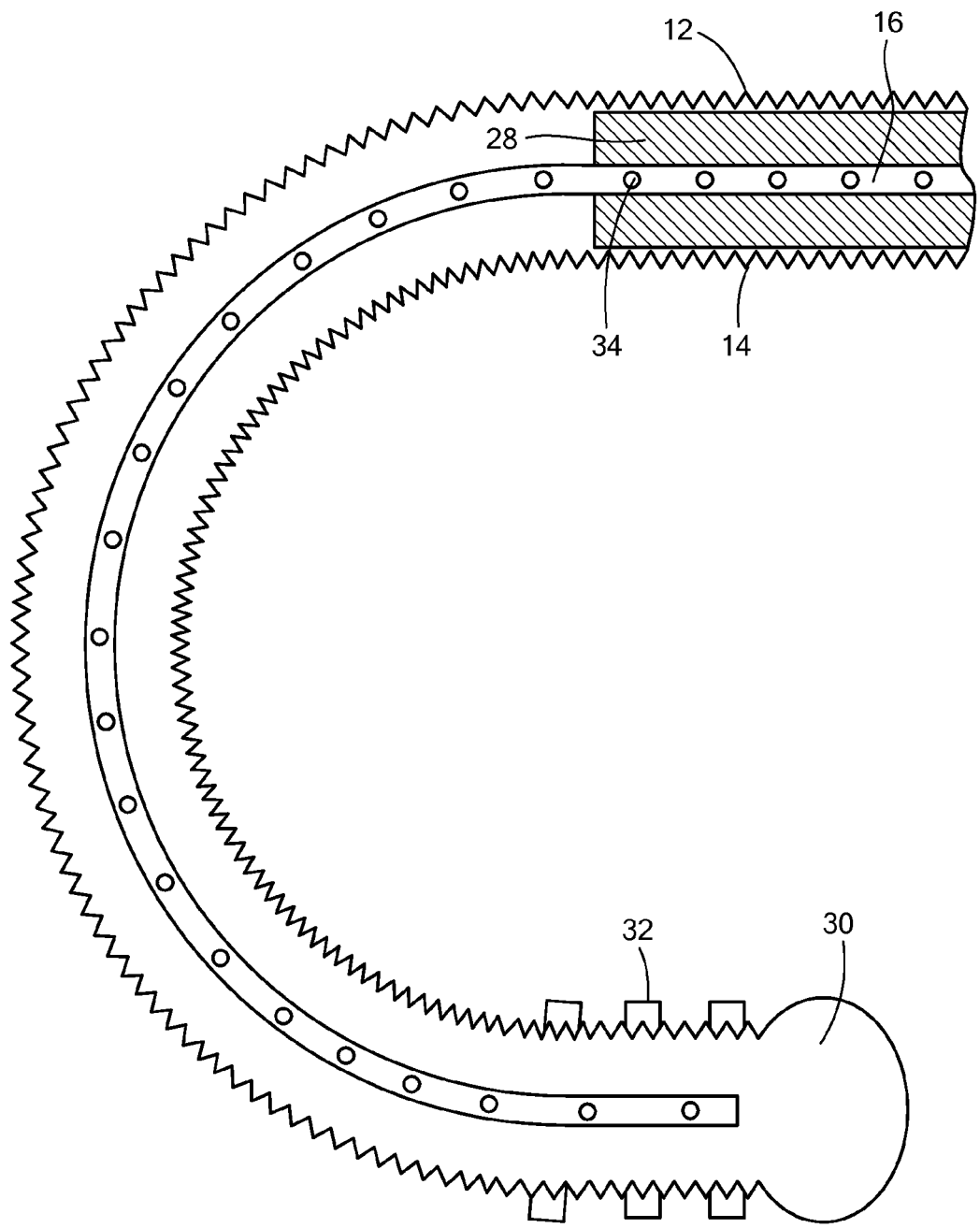
FIG. 6 is a side cross-sectional view of a sheath of the medical device in FIG. 5 being further retracted and exposing the distal tip.

Now referring to FIG. 6, the sheath 28 may be continued to be retracted from the curved geometric configuration of the treatment element 12 shown in FIG. 5 to a more arcuate geometric configuration shown in FIG. 6. In particular, it may be desirable to define the treatment element 12 as an arcuate shape to perform epicardial and/or endocardial ablation. In such a geometric configuration, the sheath 28 is retracted to a position such that the biased treatment element 12 begins to form a substantially circular configuration.

Figure 7:
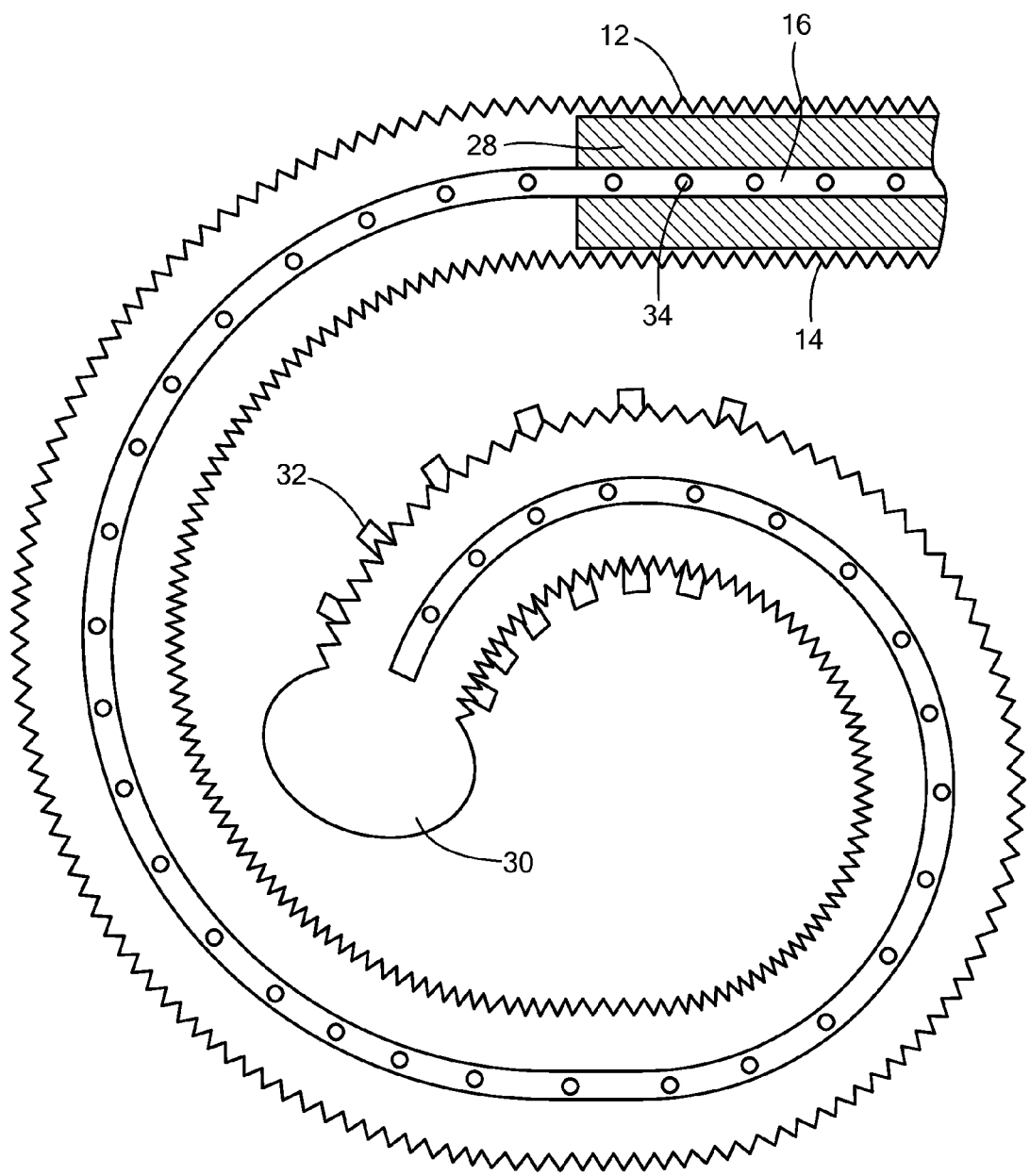
FIG. 7 is a side cross-sectional view of a sheath of the medical device in FIG. 6 being further retracted and exposing the distal tip.

Now referring to FIG. 7, when the sheath 28 is retracted to a predetermined position with respect to the treatment element 12, the treatment element 12 may transition from a substantially arcuate or curvilinear geometric configuration to a substantially circular geometric configuration. In such a configuration, the treatment element 12 may be exposed such that large-area ablation procedures may be performed. For example, the substantially circular treatment element 12 may be used to create a substantially circumferential lesion pattern on the tissue to be treated. Such lesions may be created on both the epicardium and the endocardium. Such lesions may also create contiguous lesions of a circular nature that reach beyond the circumference of the treatment element 12 and across the circumscribed diameter. Optionally, the substantially circular geometric configuration may be deployed substantially orthogonal to the configuration shown in FIG. 7 to create quasi-linear lesions.

Figure 8:
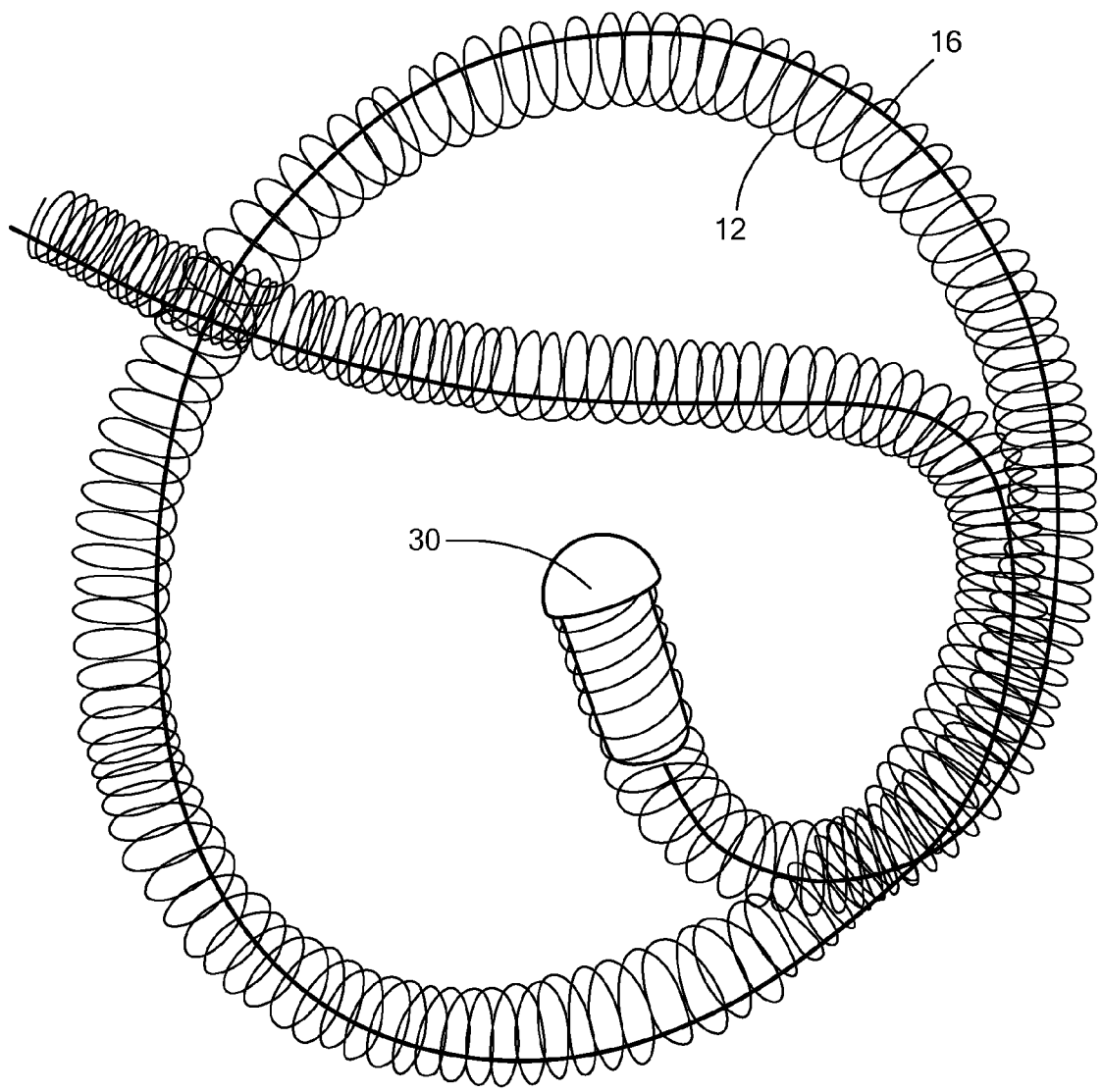
FIG. 8 is a front view of another embodiment of the medical device constructed in accordance with the principles of the present invention.

Now referring to FIG. 8, the fluid injection tube 16 may be a nitinol tube biased to transition into a substantially circular configuration. The nitinol fluid injection tube 16 may be surrounded by and in thermal communication with a thermally conductive coil 12. The coil 12 may be sufficiently flexible to conform to the shaft of the nitinol tube 16. Alternatively, the coil 12 may be biased in a substantially circular configuration, such that fluid injection tube conforms to the shape of the coil 12. As cryogenic fluid is circulated through the nitinol injection tube 16, the surrounding coil 12 is also cooled such that the coil 12 operates a cryogenic ablation element. Disposed at the distal end of the fluid injection tube 16 may be the distal tip housing the plurality of electrodes 32 to map the tissue region to be treated. In such a configuration, the nitinol fluid injection tube 16 may not include the fluid injection ports 34 such that the cryogenic fluid is retained within the injection tube. In another embodiment, the fluid injection tube 16 may include the plurality of fluid injection ports 34. The sheath 28 may surround the nitinol fluid injection tube 16 and may be disposed between the injection tube 16 and the coil 12 such that it may block the fluid injection ports 34 when disposed over them. As the sheath 28 advanced or retracted the fluid injection ports 34 may be exposed or blocked such that cryogenic fluid may be sprayed from the exposed fluid injection ports 34. As such, the freezing area of the coil 12 may be adjusted depending on the number of fluid injection ports 34 exposed to provide for a particular ablation shape and size.

Additionally, the control unit 22 may include a processor to correlate the distance the sheath 28 is advanced or retracted and the resulting treatment element 12 and/or fluid injection tube 16 shapes. The control unit 22 may monitor and measure the distance the sheath 28 is retracted in millimeters, microns or any unit. Based on the distance the sheath is retracted, and based on the pre-fabricated shape of the treatment element 12 and/or fluid injection tube 16, the control unit 22 may determine the precise shape of the treatment element 12. For example, the control unit 22 may determine that when the sheath 28 is retracted 5 millimeters, the treatment element may define, for example, a 15 degree angle with respect to the major axis defined by the sheath 28. As such, the surgeon may be able to, with precise accuracy, create a desired treatment element 12 shape without the need for pull wires and torqueing of the treatment element based on the desired lesion to be created.

Optionally, the sheath 28 and/or treatment element 12 may be equipped with tabs, notches, or other releasably securable mechanisms to lock the sheath 28 with respect to the treatment element 12 at pre-determined locations. For example, as the sheath 28 is advanced or retracted, the sheath 28 may releasable lock to a portion of the treatment element 12 such that the shape of the treatment element 12 remains fixed during a treatment procedure. This may help to ensure that accuracy in creating the desired lesion pattern. Any number of notches and tabs may be disposed along the length of the sheath 28 or treatment element 12.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   an ablation element;
   a thermally insulative sheath disposed within the ablation element;
   a fluid injection tube disposed within a portion of the thermally insulative sheath; and
   the ablation element passively transitioning from a substantially linear geometric configuration to a substantially circular geometric configuration as the sheath is retracted proximally from a first position in which the sheath substantially encloses the fluid injection tube to a second position in which a portion of the fluid injection tube extends a distance away from the sheath, at least a portion of the fluid injection tube being biased in the substantially circular geometric configuration.

2. The medical device of claim 1, wherein the ablation element is a cryogenic ablation element.

3. The medical device of claim 1, wherein fluid injection tube is composed of a shape memory material.

4. The medical device of claim 3, wherein the fluid injection tube defines a plurality of fluid injection ports.

5. The medical device of claim 1, wherein the ablation element includes a bellows portion.

6. The medical device of claim 1, further including a distal tip coupled to the ablation element, and wherein the distal tip includes plurality of electrodes.

7. The medical device of claim 1, wherein the ablation element defines a coil.

8. The medical device of claim 1, wherein the thermally insulative sheath is stiffer than the fluid injection tube.

9. The medical device of claim 1, further comprising a handle, and wherein the ablation element and the sheath are coupled to the handle.

10. The medical device of claim 9, further comprising an actuator coupled to the handle, and wherein the actuator operates to advance and retract the sheath.

11. A medical device, comprising:
    a cryogenic ablation element;
    a thermally insulative sheath disposed within the cryogenic ablation element;
    a fluid injection tube disposed within a portion of the thermally insulative sheath and in fluid communication with a cryogenic fluid source, the fluid injection tube defining a plurality of fluid injection ports;
    the sheath sealing at least one of fluid injection ports when advanced toward a distal portion of the cryogenic ablation element; and
    the cryogenic ablation element passively transitioning from a substantially linear geometric configuration to a substantially circular geometric configuration as the sheath is retracted proximally from a first position in which the sheath substantially encloses the fluid injection tube to a second position in which a portion of the fluid injection tube extends a distance away from the sheath, at least a portion of the fluid injection tube is biased in the substantially circular geometric configuration.

12. The medical device of claim 11, further including a distal tip coupled to the cryogenic ablation element, and wherein the distal tip includes plurality of electrodes.

13. The medical device of claim 11, wherein the cryogenic ablation element includes a bellows portion.

14. The medical device of claim 11, further comprising a handle, and wherein the cryogenic ablation element and the sheath are coupled to the handle.

15. The medical device of claim 14, further comprising an actuator coupled to the handle, and wherein the actuator operates to advance and retract the sheath.

16. The medical device of claim 11, wherein fluid injection tube is more flexible than the sheath.

17. The medical device of claim 11, wherein the cryogenic ablation element is passively transitionable from a substantially linear geometric configuration to a substantially curvilinear geometric configuration when the sheath is retracted.

18. A medical device, comprising:
  a cryogenic ablation element including a bellows portion;
  a thermally insulative sheath movably disposed within the cryogenic ablation element;
  a fluid injection tube disposed within a portion of the thermally insulative sheath and in fluid communication with a cryogenic fluid source, the fluid injection tube defining a plurality of fluid injection ports, and at least a portion of the fluid injection tube being biased in a substantially circular configuration;
  the sheath sealing at least one of fluid injection ports when advanced toward a distal portion of the cryogenic ablation element;
  the sheath being stiffer than the fluid injection tube; and
  the cryogenic ablation element passively transitioning from a substantially linear geometric configuration to a substantially curvilinear geometric configuration, and passively transitioning from the substantially curvilinear geometric configuration to a substantially circular geometric configuration as the sheath is retracted proximally from a first position in which the sheath substantially encloses the fluid injection tube to a second position in which a portion of the fluid injection tube extends a distance away from the sheath.

* * * * *